United States Patent [19]

Campagna, Jr. et al.

[11] Patent Number: 4,628,917

[45] Date of Patent: Dec. 16, 1986

[54] COMBINATIONS OF MATERIALS AND METHOD FOR FORMING A SPLINT

[75] Inventors: Anthony J. Campagna, Jr., Roseville; Patricia A. Eull, St. Paul; Katherine E. Reed, Grant Township, Washington County, all of Minn.

[73] Assignee: Minnesota Mining and Manufacturing Company, Saint Paul, Minn.

[21] Appl. No.: 667,271

[22] Filed: Nov. 1, 1984

[51] Int. Cl.$^4$ .............................................. A61F 5/04
[52] U.S. Cl. ...................................................... 128/90
[58] Field of Search .................... 128/90, 91 R, 87 R, 128/89 R

[56] References Cited

U.S. PATENT DOCUMENTS

| | | | |
|---|---|---|---|
| 3,985,128 | 10/1976 | Garwood et al. | 128/90 |
| 4,129,127 | 12/1978 | Ellison | 128/91 R |
| 4,235,228 | 11/1980 | Gaylord, Jr. et al. | 128/91 R |
| 4,442,833 | 4/1984 | Dahlen et al. | 128/90 |
| 4,454,874 | 6/1984 | Monnier | 128/91 |
| 4,502,479 | 3/1985 | Garwood et al. | 128/90 |

Primary Examiner—John Kight
Assistant Examiner—Kriellion Morgan
Attorney, Agent, or Firm—Donald M. Sell; James A. Smith; William L. Huebsch

[57] ABSTRACT

A combination of materials that can be used to form a splint or protective covering including a support mat including a water hardenable resin impregnated fabric with water restricting film along at least one of its major surfaces, and a pressure sensitive adhesive coated padding that can be adhered to the support mat after the fabric is exposed to water so that the resultant laminate can be applied to a person with a dry surface of the padding against his skin.

3 Claims, 6 Drawing Figures

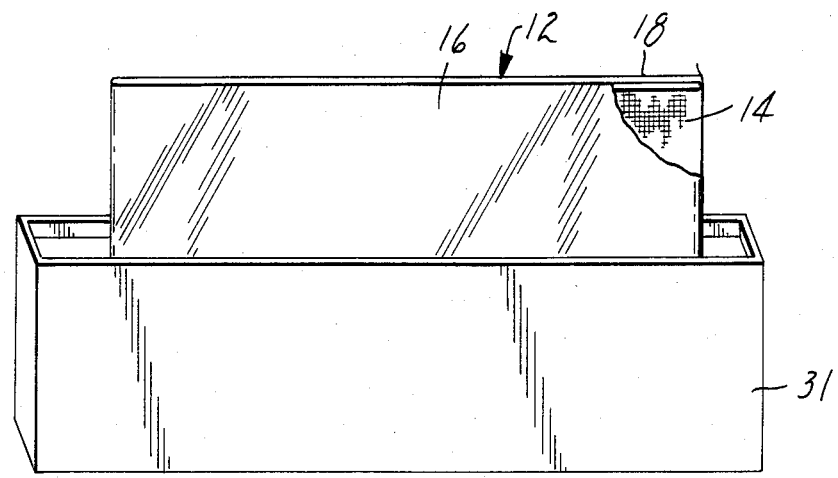
FIG. 4
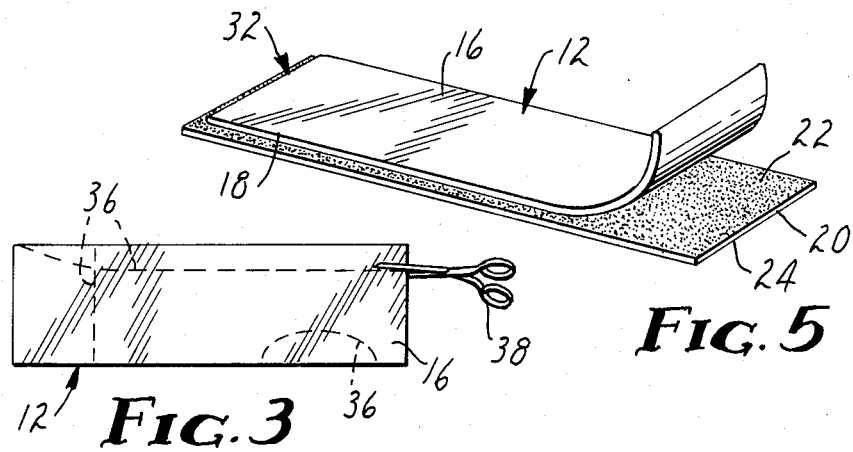
FIG. 5
FIG. 3
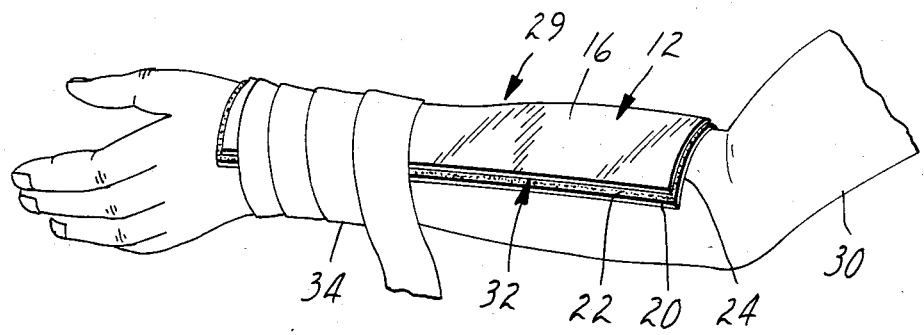
FIG. 6

COMBINATIONS OF MATERIALS AND METHOD FOR FORMING A SPLINT

FIELD OF THE INVENTION

The present invention relates to combinations of materials and methods used for forming splints.

BACKGROUND OF THE INVENTION

The prior art is replete with combinations of materials and methods for custom forming splints on a patient.

U.S. Pat. No. 4,235,228 describes such a combination of materials comprising a plaster impregnated fabric core, a layer of padding around at least one surface of the fabric and a length of tubular stockinet encircling the fabric and padding. This combination can be cut to a desired length, dipped in water to begin hardening of the plaster, attached to a patient by a bandage or other fastener and allowed to harden to form a splint.

Another similar combination of materials described in U.S. Pat. No. 4,442,833 includes an elongate support mat comprising a fabric impregnated with a curable resin that cures and hardens when exposed to water and a flexible water restricting film disposed along and covering the major surface of the fabric with edges of the fabric exposed to afford entrance of water, a layer of padding disposed along one outer surface of the film covering the fabric and a length of tubular stockinet encircling the padding and support mat. This combination of materials also may be dipped in water to begin hardening of the resin, attached to a patient by a bandage or other fastener and allowed to cure to form a splint.

While both of the combination of materials described above can form serviceable splints of various shapes, both are entirely damp when applied which is unpleasant for the patient and can provide undesirable environments for any wounds that are present on the parts of patients' bodies over which the splints are applied.

While U.S. Pat. No. 3,985,128 describes a splint that can be applied dry, that splint requires ultraviolet light to harden the splint and thus can only be used where a source of ultraviolet light is present.

DISCLOSURE OF THE INVENTION

The present invention provides a combination of materials adapted to be applied to a person to form a splint or protective covering which is made rigid by exposure to water, but which provides a dry surface to be applied to the skin of the person and affords more versatility in custom shaping the splint or protective covering than the prior art combinations of materials described above.

According to the present invention there is provided a combination of materials including: (1) an elongate flexible support mat comprising a flexible fabric impregnated with a soft curable resin that will cure and harden when exposed to water to provide rigidity for the splint or protective covering, and a flexible water restricting film disposed along and covering at least one major surrace of the fabric to afford handling the support mat without gloves to protect the user from the resin while leaving portions of the fabric exposed to afford exposure to water; and (2) a sheet of soft resilient padding coated on one major surface with pressure sensitive adhesive that will adhere to a moist surface of the support mat.

This combination of materials can be applied to a patient to form a splint by the steps of: (1) exposing the support mat to water so that water will enter the fabric through its exposed portions to initiate the hardening of the resin; (2) adhering the sheet of padding along one major surface of the support mat after the exposing step to form a laminate; (3) positioning the dry surface of the padding to opposite the support mat on the skin of a person; (4) wrapping a bandage or other fastener around the laminate and the person to secure the splint in place; and (5) allowing the resin to harden.

In addition to the major advantage of allowing the laminate to be applied with a dry surface against a person to which the splint or protective covering is to be applied, the method according to the present invention also allows the support mat to be trimmed to a desired shape prior to having the padding adhered to it, which trimming is not as easily possible with the prior art combinations described above. Also the method according to the present invention allows the use of more than one support mat which may require pealing away parts of the water restricting film on each and bringing the curable resin impregnated fabrics of the mats into face to face contact so that they will adhere together and provide a stiffer splint or covering. Thus great versatility is afforded in the shape and rigidity of a splint or covering made according to the present invention.

BRIEF DESCRIPTION OF THE DRAWING

The present invention will be further described with reference to the accompanying drawing wherein like reference numerals refer to like parts in the several views, and wherein:

FIGS. 3 through 6 illustrate sequential steps in a method according to the present invention for applying the combination of materials of FIG. 1 to form a splint or protective covering on a person.

DESCRIPTION OF THE PREFERRED EMBODIMENT

Figure 1:
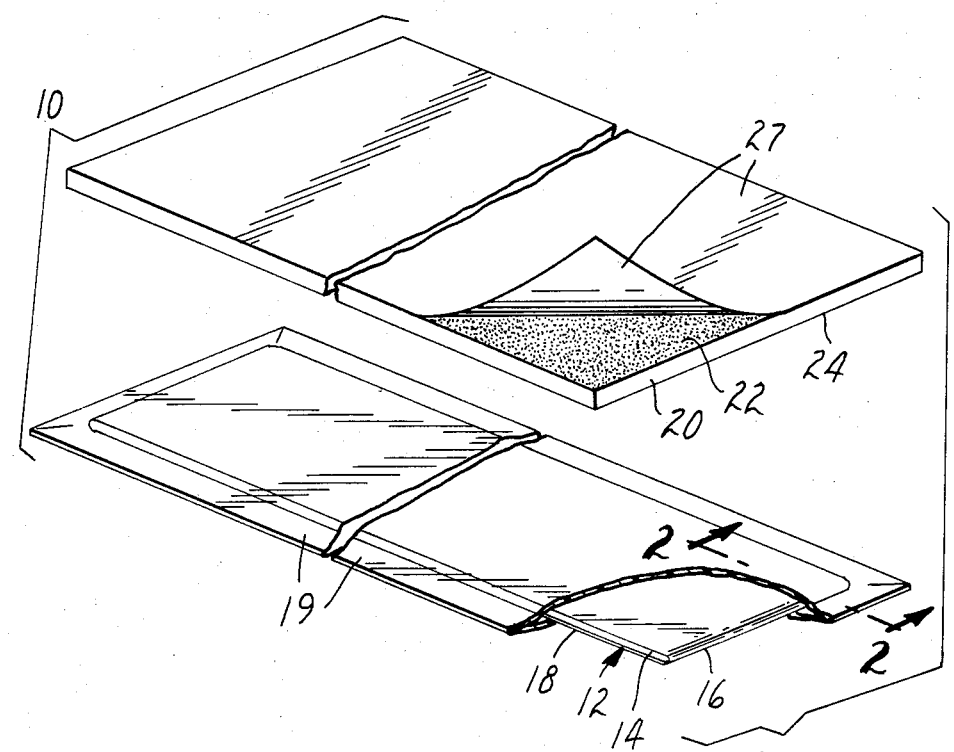
FIG. 1 is a fragmentary perspective view showing a combination of materials according to the present invention and having a part broken away to show details.

Referring now to the drawing there is shown in FIG. 1 a combination of materials according to the present invention adapted to be applied to a patient to form a splint or protective covering, which combination is generally designated by the reference numeral 10.

Figure 2:
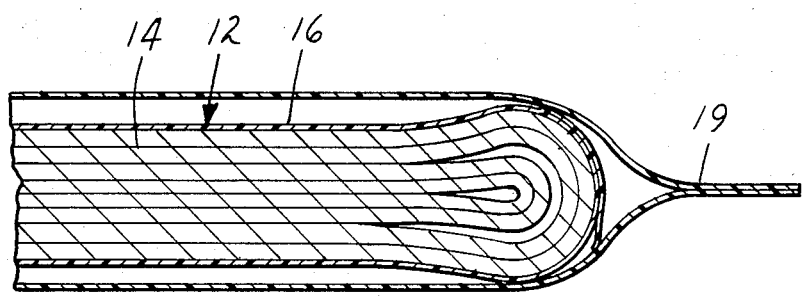
FIG. 2 is an enlarged sectional view taken approximately along line 2—2 of FIG. 1.

The combination of materials 10 shown in FIG. 1 includes an elongate flexible support mat 12 (shown in FIGS. 1 and 2) comprising a flexible fabric 14 impregnated with a soft curable resin that will cure and harden to provide rigidity for the splint or covering upon exposure to water, and a flexible water restricting film 16 disposed along and covering the major surfaces and ends of the fabric 14 to afford handling of the support mat 12 without the use of gloves for protection from the curable resin while the film 16 has spaced longitudinal edges which leave the longitudinal edge portions 18 of the fabric 14 exposed to afford exposure of the fabric 14 to water. The support mat 12 is initially enclosed in a bag 19 of water vapor impervious material (e.g., metal foil) to restrict hardening of the resin due to water absorption from the air. Also included in the combination of materials 10 is a sheet 20 of soft resilient padding (FIG. 1) having opposite major surfaces 22 and 24, and a coating of pressure sensitive adhesive on the major surface 22 of the sheet 20 that will adhere to a moist surface of the water restricting film 16 or the fabric 14. The coating of pressure sensitive adhesive is initially protected by a removable release liner 27.

As illustrated in FIGS. 3 through 6, the method according to the present invention for applying a splint 29 to a person or patient 30 (FIG. 6) using the combination of materials 10 shown in FIG. 1 comprises the steps of (1) exposing the support mat 12 to water (after removing it from the bag 19) such as by dipping the support mat 12 in water in a tank 31 (FIG. 4) so that the water will enter the fabric 14 through its edge portions 18 to initiate the hardening of the resin; (2) adhering the sheet 20 of resilient foam padding to one major surface of the support mat 12 after the exposing step and removal of the liner 27 to form a laminate 32 (FIG. 5); (3) positioning the dry surface 24 of the sheet 20 of padding opposite the support mat 12 on the surface of the person 30 (FIG. 6); (4) attaching the laminate 32 to the patient 30 by wrapping a bandage 34 or other fastener around the laminate 32 and patient 30 (FIG. 6); and (5) allowing the resin to harden.

Additionally, as illustrated in FIG. 3, the method may further comprise the step of trimming the support mat 12 to a desired shape such as along the dotted lines 36 through the use of a scissors 38, which trimming preferably is done prior to the time the support mat 12 is dipped in water and/or adhered to the support sheet 20 of padding.

Preferably the support mat 12 comprises several face to face layers of the material designated "SCOTCHCAST" (RTM) 2 Casting Tape and sold by Minnesota Mining and Manufacturing Company, St. Paul, Minn., which casting tape comprises a knit fiberglass fabric 14 impregnated with a curable polyurethane resin which is soft, flexible and compliant, and will harden to produce a stiff structure in a time period of about five minutes when contacted by water. Also, preferably, the film 16 is a stretchable polyurethane film about 0.003 centimeter thick which restricts the passage of liquid water but will transmit water vapor, the film 16 being adhered to the fabric 14 by the polyurethane resin in the fabric 14 both in the soft and hardened states of the resin.

The sheet 20 of padding is preferably the open cell polyurethane foam sold under the trade designation "RESTON" (RTM) Self Adhering Foam Roll, by Minnesota Mining and Manufacturing Company, St. Paul, Minn., which foam has on one surface a coating of acrylate pressure sensitive adhesive that will adhere moderately well to moist surfaces.

The combination of materials and method according to the present invention have now been described with reference to preferred embodiments thereof. It will be appreciated by those skilled in the art that certain substitutions of materials and the use of slightly modified method steps are possible without departing from the spirit of the invention. For example, exposing the support mat 12 to water can occur by absorption of water from the atmosphere at normal levels of relative humidity if a long resin cure time (e.g. 12 hours) is permissible. Also only one major surface of the fabric 12 may be covered by the film 16 which will still permit handling of the support mat 12 without gloves, in which case the sheet 20 of padding will preferably be adhered to the non-film covered major surface of the support mat 12 to restrict contact with the curable resin. Thus, the scope of the present invention should not be limited to the structures and method steps described in this application, but only to structures and method steps described by and included in the language of the claims and their equivalents.

We claim:

1. A method for applying a splint or protective covering to a person comprising the steps of:

providing an elongate support mat including a flexible fabric impregnated with a soft curable resin that hardens upon exposure to water, which fabric has two opposite major surfaces and a flexible water restricting film disposed along and covering at least one major surface of said fabric while leaving portions of the fabric exposed, and a sheet of soft resilient padding having opposite major surfaces and coated along one major surface with a pressure sensitive adhesive that will adhere to a moist surface;

exposing the support mat to water so that water will enter the fabric through its exposed portions to initiate the hardening of the resin;

adhering the sheet of resilient padding to one major surface of the support mat after the exposing step to form a laminate;

positioning the dry surface of the padding opposite the support mat on the skin of the person;

attaching the laminate to the person to secure the splint or protective covering in place; and allowing the resin to harden.

2. A method according to claim 1 wherein said method further comprises the step of trimming the support mat to shape prior to said adhering step.

3. A combination of materials adapted to be applied to a patient to form a splint or protective covering, said combination of materials comprising:

an elongate flexible support mat including a flexible fabric impregnated with a soft curable resin that will harden upon exposure to water and having opposite major surfaces, and a flexible water restricting film disposed along and covering at least one major surface of said fabric while leaving portions of the fabric exposed; and a sheet of soft resilient padding having opposite major surfaces, and a coating of pressure sensitive adhesive that will adhere to a moist surface on one major surface of said padding so that to form a splint, said support mat may be exposed to water to initiate hardening of the resin, and the sheet of resilient padding may then be adhered along one major surface of the support mat to form a flexible laminate having a dry surface of the padding that can be applied against the skin of a person to form a splint or protective covering upon hardening of the resin.

* * * * *